United States Patent [19]

Franckowiak et al.

[11] Patent Number: 5,344,944
[45] Date of Patent: Sep. 6, 1994

[54] CIRCULATION-ACTIVE DIOXYALKYLENEARYL-DIHYDROPYRIDINES

[75] Inventors: Gerhard Franckowiak, Wuppertal; Albrecht Marhold, Leverkusen; Martin Bechem; Rainer Gross, both of Wuppertal; Michael Kayser; Matthias Schramm, both of Leverkusen; Günther Thomas, Wuppertal, all of Fed. Rep. of Germany

[73] Assignee: Bayer Aktiengesellschaft, Leverkusen, Fed. Rep. of Germany

[21] Appl. No.: 116,414

[22] Filed: Sep. 3, 1993

Related U.S. Application Data

[60] Continuation-in-part of Ser. No. 814,213, Dec. 19, 1991, abandoned, which is a continuation of Ser. No. 644,857, Jan. 22, 1991, abandoned, which is a continuation of Ser. No. 431,942, Nov. 6, 1989, abandoned, which is a division of Ser. No. 190,748, May 5, 1988, Pat. No. 4,886,816.

[30] Foreign Application Priority Data

May 19, 1987 [DE] Fed. Rep. of Germany ....... 3716652

[51] Int. Cl.⁵ ............................................ C07D 317/62
[52] U.S. Cl. ...................................... 549/436; 549/362
[58] Field of Search ........................................ 549/436

[56] References Cited

U.S. PATENT DOCUMENTS 4,596,880  6/1986  Lantzsch et al. .................... 549/362
4,705,800  11/1987  Nyfeler et al. ...................... 514/422

Primary Examiner—Nicky Chan
Attorney, Agent, or Firm—Sprung Horn Kramer & Woods

[57] ABSTRACT

Circulation-active dihydropyridines of the formula

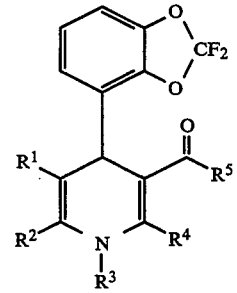

in which
$R^1$ is H, CN, $NO_2$ or —$COOR^7$,
$R^7$ is H, alkyl or various other radicals,
$R^2$ and $R^4$ each independently is alkyl or other radicals,
$R^3$ is H or optionally substituted alkyl, and
$R^5$ completes a keto or ester group, and physiologically acceptable salts thereof. Also the aldehyde intermediate therefor of the formula

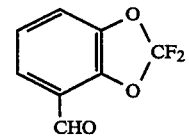

1 Claim, No Drawings

CIRCULATION-ACTIVE DIOXYALKYLENEARYL-DIHYDROPYRIDINES

This application is a continuation-in-part of application Ser. No. 814,213, filed Dec. 19, 1991, abandoned, which is a continuation of application Ser. No. 644,857, filed Jan. 22, 1991, now abandoned, which is a continuation of application Ser. No. 431,942, filed Nov. 6, 1989, now abandoned, which is a division of application Ser. No. 190,748, filed May 5, 1988, now U.S. Pat. No. 4,886,816.

The invention relates to new dioxyalkylenearyldihydropyridines, intermediate products for their preparation, processes for their preparation and their use in medicaments, in particular in medicaments which influence the circulation.

The present invention relates to dioxyalkylenearyl-dihydropyridines of the general formula (I)

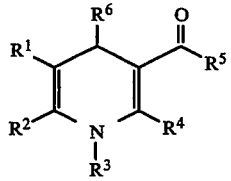

in which $R^1$ represents hydrogen, cyano or nitro, or represents a radical of the formula $-CO_2R^7$,
wherein $R^7$ denotes hydrogen or straight-chain, branched or cyclic alkyl or alkenyl which has up to 16 carbon atoms and is optionally interrupted in the chain by an oxygen atom or a sulphur atom and/or optionally substituted by one or more identical or different substituents from the group comprising halogen, cyano, hydroxyl, $C_2$–$C_7$-acyloxy and nitro or by a phenyl, phenoxy, phenylthio or phenylsulphonyl group which is optionally substituted by halogen, cyano, di-$C_1$–$C_5$-alkylamino, $C_1$–$C_6$-alkyl, $C_1$–$C_6$-alkoxy, trifluoromethyl or nitro, or by a heteroaryl group of the series comprising pyridyl, thienyl, furyl, quinolyl or pyrimidyl, or by an amino group, this amino group carrying two identical or different substituents from the group comprising $C_1$–$C_6$-alkyl, $C_6$–$C_{12}$-aryl and $C_7$–$C_{14}$-aralkyl, or it being possible for these substituents, together with the nitrogen atom, optionally to form a 5- to 7- membered ring which can contain, as a further hereto atom, a sulphur or oxygen atom or the N-phenyl or N-alkyl grouping, it being possible for the alkyl group to contain up to 4 carbon atoms, or wherein $R^7$ represents a direct bond to $R^2$ (where $R^2 \neq$ cyano, phenyl or formyl), $R^2$ and $R^4$ are identical or different and in each case represent straight-chain, branched or cyclic alkyl with up to 8 carbon atoms, or represent phenyl or benzyl, or one of the substituents $R^2$ or $R^4$ represents straight-chain or branched alkyl which has up to 6 carbon atoms and is substituted by halogen, $C_2$–$C_7$-acyloxy, hydroxyl, amino, phthalimido, alkoxy, dialkoxy, aminoalkoxy, phthalimidoalkoxy, piperidinoalkyl, morpholinoalkoxy or N-phenyl-N-piperazinoalkoxy with in each case up to 6 carbon atoms per alkoxy group, or represents formyl or cyano, $R^3$ represents hydrogen, or represents straight-chain or branched alkyl which has up to 4 carbon atoms and is optionally interrupted in the chain by an oxygen atom and/or is optionally substituted by a piperidino or morpholino radical or by phenyl, $R^5$ represents straight-chain, branched or cyclic alkyl with up to 8 carbon atoms, or represents a group $-OR^8$, wherein $R^8$ denotes hydrogen or straight-chain, branched or cyclic alkyl or alkenyl which has up to 16 carbon atoms and is optionally interrupted in the chain by an oxygen atom or a sulphur atom and/or is optionally substituted by one or more identical or different substituents from the group comprising halogen, cyano, hydroxyl, $C_2$–$C_7$-acyloxy and nitro, or by a group of the formula

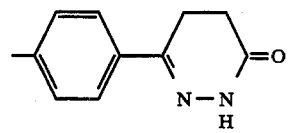

or by a phenyl, phenoxy, phenylthio or phenylsulphonyl group which is optionally substituted by halogen, cyano, di-$C_1C_5$-alkylamino, $C_1$–$C_6$-alkoxy, $C_1$–$C_6$-alkyl, trifluoromethyl or nitro, or by a heteroaryl group of the series comprising pyridyl, thienyl, furyl, quinolyl and pyrimidyl, or by an amino group, this amino group carrying two identical or different substituents from the group comprising $C_1$–$C_6$-alkyl, $C_6$–$C_{14}$-aryl and $C_7$–$C_{14}$-aralkyl, or it being possible for these substituents, together with the nitrogen atom, optionally to form a 5- to 7-membered ring, which can contain, as a further hetero atom, an oxygen or sulphur atom or the N-phenyl or N-alkyl grouping, it being possible for the alkyl group to contain up to 4 carbon atoms, and $R^6$ represents a group of the formula

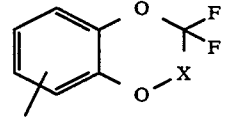

wherein

X denotes a direct bond or $-CF_2-$ or $-CHF-$, and physiologically acceptable salts thereof.

Preferred compounds of the general formula (I) are those in which $R^1$ represents hydrogen, nitro or a radical of the formula $-CO_2R^7$,
wherein $R^7$ denotes hydrogen or straight-chain or branched alkyl which has up to 12 carbon atoms and is optionally interrupted in the chain by an oxygen atom and/or is optionally mono- or polysubstituted by fluorine, chlorine, bromine, cyano, hydroxyl or acetoxy, or by a phenyl or phenoxy group which is optionally substituted by fluorine, chlorine, bromine, iodine, cyano, nitro, $C_1$–$C_4$-alkyl, $C_1$–$C_4$-alkoxy or trifluoromethyl, or by an α-, β- or γ-pyridyl group, or by an amino group, this amino group carrying two identical or different substituents from the series comprising $C_1$–$C_4$-alkyl, phenyl and benzyl, or $R^7$ represents a direct bond to $R^2$ (where $R^2 \neq$ phenyl), $R^2$ and $R^4$ are identical or different and in each case represent straight-chain or branched alkyl with up to 6 carbon atoms, or represent phenyl or benzyl, or one of the substituents $R^2$ or $R^4$ represents straight-chain or branched alkyl which has up to 4 carbon atoms and is optionally mono- or polysubstituted by fluorine, chlorine, bromine, acetoxy, benzoyloxy, methoxy, hydroxyl, amino, phthalimido, aminoalkoxy or phthalimidoalkoxy with in each case up to 4 carbon atoms per alkoxy group, $R^3$ represents hydrogen, or represents straight-chain or branched alkyl which has up to 4 carbon atoms and is optionally substituted by morpholino or phenyl, $R^5$ represents straight-chain or branched alkyl with up to 4 carbon atoms, or represents the group —$OR^8$, wherein $R^8$ denotes hydrogen or straight-chain or branched alkyl which has up to 12 carbon atoms and is optionally interrupted in the chain by an oxygen atom and/or is optionally substituted by one or more substituents from the group comprising fluorine, chlorine, bromine, cyano, hydroxyl and acetyloxy, or by the group of the formula

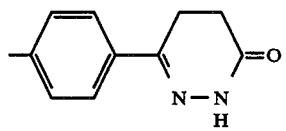

or by a phenyl or phenoxy group which is optionally substituted by fluorine, chlorine, bromine, iodine, cyano, nitro, $C_1$-$C_4$-alkyl, $C_1$-$C_4$-alkoxy or trifluoromethyl, or by an α-, β- or γ-pyridyl group, or by an amino group, this amino group carrying two identical or different substituents from the series comprising $C_1$-$C_4$-alkyl, phenyl and benzyl, and $R^6$ represents a group of the formula

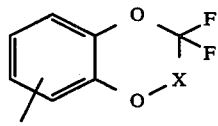

wherein

X denotes a direct bond or —$CF_2$— or —CHF—, and physiologically acceptable salts thereof.

Particularly preferred compounds of the general formula (I) are those in which $R^1$ represents nitro or a group of the formula —$CO_2R^7$, wherein $R^7$ denotes hydrogen or straight-chain or branched alkyl which is has up to 8 carbon atoms and is optionally interrupted in the chain by an oxygen atom and/or is optionally substituted by up to 15 fluorine atoms, by chlorine, cyano, acetoxy, phenyl, phenoxy or α-, β- or γ-pyridyl, or by an amino group, this amino group carrying two identical or different substituents from the group comprising $C_1$-$C_4$-alkyl and benzyl, or $R^7$ represents a direct bond to $R^2$ (where $R^2 \neq$ phenyl), $R^2$ and R are identical or different and in each case represent straight-chain or branched alkyl with up to 4 carbon atoms, or represent pyridyl, or one of the substituents $R^2$ or $R^4$ represents alkyl which has up to 2 carbon atoms and is optionally substituted by up to 3 fluorine atoms or by chlorine, bromine, acetoxy, benzoyloxy, hydroxyl or aminoethoxy, $R^3$ represents hydrogen, $R^5$ represents the group —$OR^8$, wherein $R^8$ denotes hydrogen or straight-chain or branched alkyl which has up to 8 carbon atoms and is optionally interrupted in the chain by an oxygen atom and/or is optionally substituted by up to 15 fluorine atoms, or by chlorine, cyano or acetoxy, or by the group of the formula

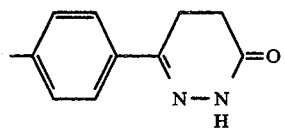

or by phenyl, phenoxy or α-, β- or γ-pyridyl, or by an amino group, this amino group carrying two identical or different substituents from the series comprising $C_1$-$C_4$-alkyl and benzyl, and $R^6$ represents a group of the formula

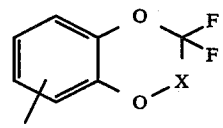

wherein

X represents a direct bond, or represents the groups —$CF_2$— or —CHF—, and physiologically acceptable salts thereof.

Physiologically acceptable salts can be salts of the compounds according to the invention with inorganic or organic acids. Examples which may be mentioned are: hydrohalides, such as, for example, hydrochlorides and hydrobromides, bisulphates, sulphates, hydrogen phosphates or phosphates, or acetates, maleares, fumarates, titrates, tartrates, lactates or benzoates.

The compounds according to the invention exist in stereoisomeric forms which either behave as mirror images (enantiomers) or do not behave as mirror images (diastereomers). The invention relates both to the antipodes and to the racemic forms as well as to the diastereomer mixtures. The racemic forms, like the diastereomers, can be resolved into the stereoisomerically uniform constituents in a known manner (compare E. L. Eliel, Stereochemistry of Carbon Compounds, McGraw Hill, 1962).

The compounds according to the invention are new and have useful pharmacological properties. They influence the blood pressure and can thus be used for combating circulatory diseases.

The compounds of the general formula (I) according to the invention in which $R^1$-$R^6$ have the meaning given, are obtained by a process in which [A] aldehydes of the general formula (II)

in which $R^6$ has the meaning given, and ketones of the general formula (III)

in which $R^1$ and $R^2$ have the meaning given, or Knoevenagel condensation products thereof (ylidene compounds) of the general formula (IV)

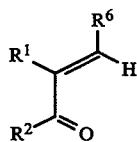

(IV)

in which

R$^1$, R$^2$ and R$^6$ have the abovementioned meaning, are reacted with enamines of the general formula (V)

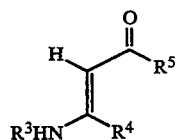

(V)

in which

R$^3$-R$^5$ have the meaning given, in inert solvents, or by a process in which [B] aldehydes of the general formula (II) and ketones of the general formula (VI)

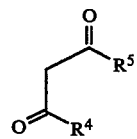

(VI)

in which

R$^4$ and R$^5$ have the meaning given, or Knoevenagel condensation products thereof (ylidene compounds) of the general formula (VII)

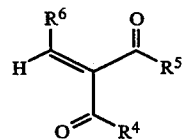

(VII)

in which

R$^4$, R$^5$ and R$^6$ have the abovementioned meaning, are reacted with enamines of the general formula (VIII)

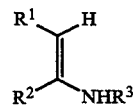

(VIII)

in which

R$^1$, R$^2$ and R$^3$ have the abovementioned meaning, in inert solvents, and, in the case where R$^2$ represents a direct bond to R$^7$, the resulting dihydropyridines are cyclized to lactones.

In the case where the radicals R$^1$, R$^3$, R$^5$, R$^6$, R$^7$, R$^8$ and X in the general formula I have the abovementioned meaning and R$^2$ or R$^4$ represents the formyl or the nitrile group or represents an alkyl radical which is substituted by hydroxyl, amino or aminoalkoxy, the compounds according to the invention are preferably prepared by a process in which suitable intermediate products according to the invention are synthesized and these are further reacted in subsequent reactions. For example, if R$^2$ or R$^4$ represents a formyl group, these derivatives are obtained by acid hydrolysis of compounds of the general formula I according to the invention in which R$^2$ or R$^4$ denotes a dialkoxymethyl radical. The derivatives of the general formula I according to the invention with R$^2$ and/or R$^4$ being nitrile are obtained by reacting the aldehydes with hydroxylamine to the oximes which are converted into the substances of the general formula I according to the invention by subsequent dehydration of the resulting oxime by methods which are known from the literature.

The compounds of the general formula I according to the invention in which R$^2$ or R$^4$ represents an alkyl radical which is substituted by a) hydroxyl, b) amino or c) aminoalkoxy are obtained in a similar manner by a process in which a) the corresponding acyloxy derivatives according to the invention are subjected to acid or alkaline hydrolysis, b) the corresponding phthalimido compounds which can be prepared by processes described above are hydrazinolyzed, for example, or c) the corresponding phthalimidoalkoxy derivatives according to the invention are reacted with hydrazine.

Depending on the nature of the starting substances used, the synthesis variants for the compounds according to the invention can be represented by the following equations:

[A]

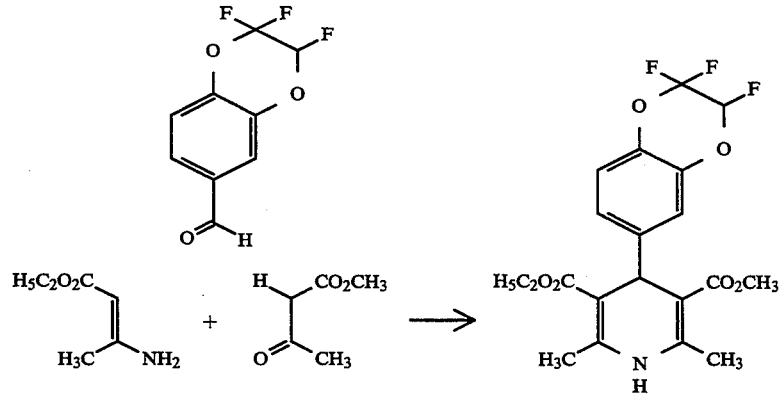

or

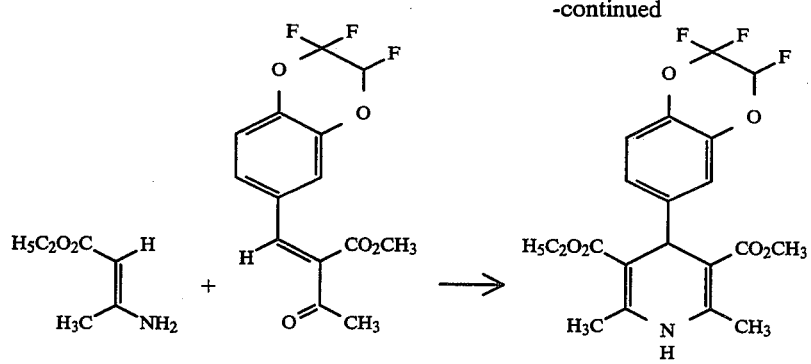

[B]

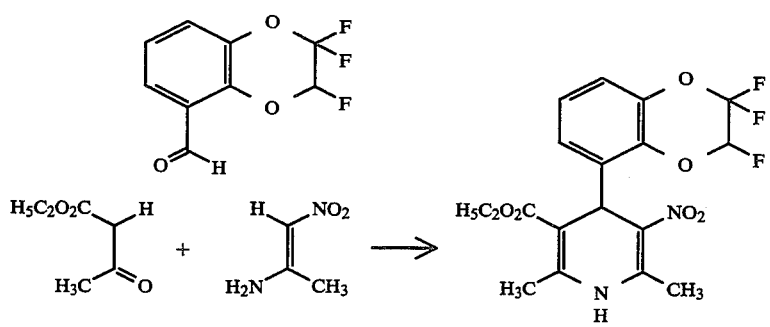

or

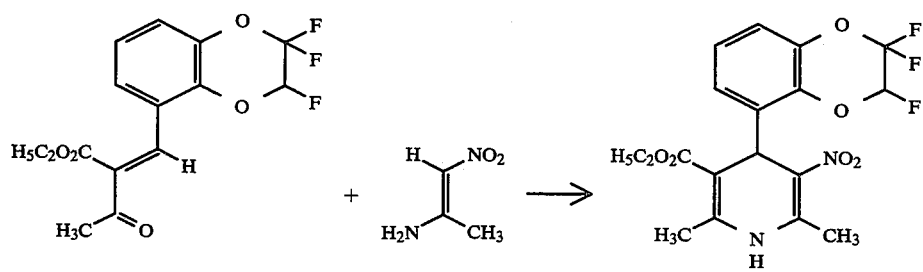

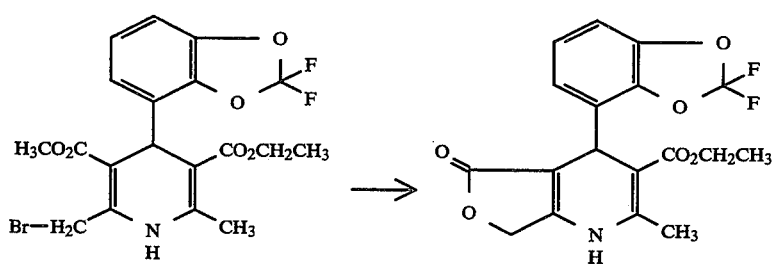

Process Variants A and B

Possible solvents for process variants A and B according to the invention are all the inert organic solvents. These include, preferably, alcohols, such as ethanol, methanol or isopropanol, ethers, such as dioxane, diethyl ether, tetrahydrofuran, glycol monomethyl ether or glycol dimethyl ether, or glacial acetic acid, dimethylformamide, dimethylsulphoxide, acetonitrile, pyridine or hexamethyl phosphoric acid triamide.

The reaction temperatures can be varied within a substantial range. The reaction is in general carried out between +20° C. and +150° C., preferably between +20° C. and +100° C., and in particular at the boiling point of the particular solvent.

The reaction can be carried out under normal pressure, but also under increased or reduced pressure. The reaction is in general carried out under normal pressure.

In carrying out processes A and B according to the invention, the substances participating in the reaction are preferably each employed in molar amounts.

The cyclization of the dihydropyridines to lactones can be carried out by a procedure in which those dihydropyridines in which $R^3$ represents an acyloxymethyl radical are cyclized in inert solvents, if appropriate in the presence of bases, or by a procedure in which those dihydropyridines in which $R^3$ represents a halogenomethyl radical are pyrolyzed with or without solvents.

Suitable bases for the cyclization are the customary bases, such as, for example, alkali metal or alkaline earth metal hydroxides, in particular sodium, potassium or calcium hydroxide, or amine, such as ammonia, triethylamine or pyridine. The cyclization can be carried out in the customary solvents, such as aromatic hydrocarbons (for example benzene or toluene), alcohols (for example ethanol, propanol or methanol) or acetic acid. The cyclization is carried out at temperatures from +10° C. to +200° C., preferably from +20° C. to +150° C.

The pyrolysis can be carried out with or without solvents. Possible solvents are, where appropriate, all the customary inert organic solvents. These include, preferably, hydrocarbons, such as benzene, toluene or xylene, tetralin, petroleum fractions, ethers, such as diethyl ether, dioxane, tetrahydrofuran or glycol mono- or diethyl ether, or halogenohydrocarbons, such as methylene dichloride, chloroform, carbon tetrachloride or di- chloro- or trichloroethylene.

The pyrolysis is carried out in a temperature range from +20° C. to +300° C., preferably from +40° C. to +250° C.

The pyrolysis can be carried out under normal, increased or reduced pressure. The pyrolysis is in general carried out under normal pressure. Process F is preferred.

The aldehydes of the general formula (II)

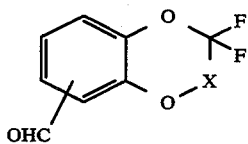

in which

X represents a direct bond, or represents a group of the formula —CF$_2$— or —CHF— excluding the compound 2,2-difluoro-5-formyl-1,3-benzodioxole, are new and can be prepared by a process in which [C] methyl-substituted compounds of the general formula (IX)

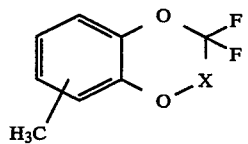

in which

X has the abovementioned meaning, are reacted with halogenating agents in inert solvents, if appropriate in the presence of agents which form free radicals, and the halogenomethyl compounds of the general formula (X)

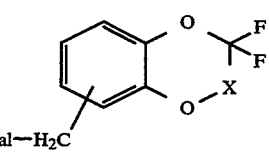

in which

X has the abovementioned meaning and Hal represents halogen, preferably chlorine or bromine, are then treated with urotropin in inert solvents, if appropriate in the presence of acids, or by a process in which [D] amino compounds of the general formula (XI)

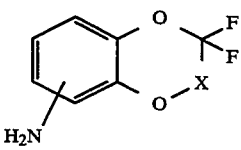

in which

X has the abovementioned meaning, are reacted with nitrites in inert solvents in the presence of acids, and the resulting diazonium salts are then reacted with formaldoxime.

The processes according to the invention can be illustrated by the following equations:

[C]
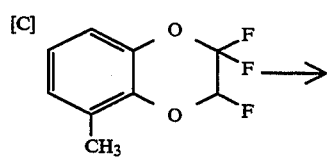

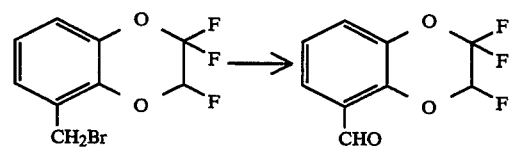

[D]
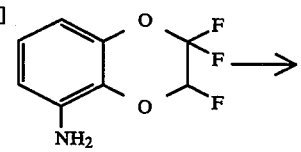

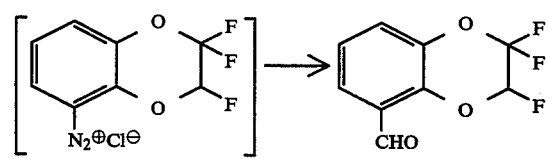

Process Variant C

Suitable solvents for this are all the inert organic solvents which do not change under the reaction conditions. These include, preferably, halogenohydrocarbons, such as, for example, methylene chloride, chloroform or carbon tetrachloride, or hydrocarbons, such as benzene, toluene or xylene, or glacial acetic acid.

The generally customary halogenating agents can be used as the halogenating agents. Preferred halogenating agents are chlorine, bromine, N-chlorosuccinimide (NCS) or N-bromosuccinimide (NBS), if appropriate in the presence of agents which form free radicals, such as azobisisobutyronitrile (AIBN), benzoyl peroxide, Porofor-N or light. Bromination with NBS or Porofor-N in carbon tetrachloride is particularly preferred.

The reaction temperatures can in general be varied within a substantial range. The reaction is preferably carried out in a range from −10° C. to +100° C., preferably from 0° to +80° C.

The reaction can be carried out under normal pressure, but also under increased or under reduced pressure. The reaction is in general carried out under normal pressure.

In general, any ratio of the amounts of reactants can be chosen. However, the reaction is preferably carried out with an amount of 1 to 5 mol, particularly preferably 1 mol, of the halogenating agent per mol of the methyl-substituted compound.

The reaction of the bromomethyl compound with urotropin in the second step of process variant C according to the invention is in general carried out in water or organic solvents, such as alcohols, preferably methanol, ethanol, propanol or isopropanol, or mixtures thereof, in the presence of an acid, preferably an inorganic mineral acid, such as, for example, hydrochloric acid, hydrobromic acid or sulphuric acid. The process is preferably carried out in water in the presence of hydrochloric acid.

The reaction is in general carried out in a temperature range from 0° C. to +150° C., preferably from +20° C. to +100° C.

The reaction can be carried out under normal pressure, but also under increased or reduced pressure. The reaction is in general carried out under normal pressure.

The reaction mixture is worked up in accordance with customary methods by distillation (preferably steam distillation), crystallization and/or chromatography.

The methyl-substituted compounds of the general formula (IX) used as starting substances are known or can be prepared by known methods.

Process Variant D

In carrying out process variant D according to the invention, the diazonium salts are in general formed as intermediate products. It has proved appropriate here to carry out the process without isolating the intermediate products.

Suitable solvents here are water or alcohols, such as methanol, ethanol, propanol or isopropanol, or amides, such as dimethylformamide or dimethylacetamide, or acids, such as mineral acids or carboxylic acids. Water and/or acids, such as hydrochloric acid, hydrobromic acid, sulphuric acid, phosphoric acid or acetic acid, are preferred. It is also possible to use mixtures of the solvents mentioned.

The acids used are in general mineral acids. Hydrochloric acid, hydrobromic acid, sulphuric acid, phosphoric acid or mixtures of the acids mentioned are preferred here.

The diazotization is particularly preferably carried out in a mixture of water and concentrated hydrochloric acid.

The nitrites used are in general alkyl nitrites, such as, for example, sodium or potassium nitrite. Sodium nitrite is preferably used.

Process variant D according to the invention is in general carried out by first preparing a solution of the diazonium salts which are reacted with formaldoxime in a second step.

The reaction is in general carried out in a temperature range from −10° C. to +100° C., preferably from 0° C. to +80° C.

The reaction is in general carried out under normal pressure. It is also possible to carry out the reaction under increased or reduced pressure.

The amines of the general formula (XI) used as starting substances are known or can be prepared by known methods [European Patent Specification 11,179].

The ketones of the general formula III or VI used as starting substances can be prepared by known methods [compare, for example, D. Borrmann, "Umsetzung von Diketen mit Alkoholen, Phenolen und Mercaptanen" ("Reaction of diketene with alcohols, phenols and mercaptans"), in Houben-Weyl's "Methoden der Organischen Chemie" ("Methods of Organic Chemistry"), Volume VII/4, 230 et seq. (1968); Y. Oikawa, K. Sugano and O. Yonemitsu, J. Org. Chem. 43, 2087 (1978); N. Levy, C. W. Scaife, J. Chem. Soc. (London) 1946, 1100; C. D. Hurd, M. W. Nilson, J. Org. Chem. 20, 927 (1955); S. Gelin, P. Poller Synth. Commun. 1980, 805 and Tetrahedron 34, 1453 (1978); G. F. Field, W. J. Zally, Synthesis 1979, 295].

The enamines of the general formula V or VIII used as starting substances are known or can be prepared by known methods [compare, for example, A. C. Cope, J. Am. Soc. 67, 1017 (1945); H. Böhme, K.-H. Weisel, Arch. Pharm. 310, 30 (1977)].

The above preparation processes are given merely for illustration. The preparation of the compounds of the formula I is not limited to these processes, but any modification of these processes can be used in the same way for the preparation of the compounds according to the invention.

The compounds according to the invention influence the contraction force of the heart and the tone of the smooth muscle. They can therefore be used in medicaments for influencing pathologically changed blood pressure, as coronary therapeutics and for the treatment of cardiac insufficiency. They can moreover be used for the treatment of disorders in cardiac rhythm, for reducing the blood sugar, for detumescing mucous membranes and for influencing the salt and fluid balance.

The cardiac and vascular actions were found on the guinea-pig heart perfused in isolation.

For this, the hearts of guinea-pigs weighing 250 to 350 g are used. The thorax is opened and a metal canula is inserted into the exposed aorta. The heart is removed from the thorax with the lungs and is connected via an aorta canula to the perfusion apparatus with the perfusion running. The lungs are detached at the roots of the lungs. The perfusion medium used is a Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$ and 0,013 mmol/l of $Na_2EDTA$), the $CaCl_2$ content of which is 1.2 mmol/l. 10 mmol/l of glucose are added as the substrate which supplies energy. The solution is filtered free from particles before the perfusion. The solution is gassed with carbogen (95% $O_2$, 5% $CO_2$) to maintain the pH at 7.4. The hearts are perfused at a constant flow (10 ml/minute) at 32° C. by means of a roller squeeze pump.

To measure the cardiac function, a latex balloon filled with liquid and connected via a column of liquid to a pressure transducer is inserted through the left auricle into the left ventricle, and the isovolumetric contractions are recorded on a high-speed recorder (Opie, L., J. Physiol. 180 (1965), 529–541). Under these conditions, a reduction in the perfusion pressure indicates coronary dilation, and an increase or decrease in the left ventricular contraction amplitude indicates an increase or reduction in the contractility of the heart. The compounds according to the invention are in fused in suitable dilutions into the perfusion medium shortly before the isolated heart.

The following values show, by way of example, the effect of the compounds according to the invention on the guineapig heart perfused in isolation, expressed as the percentage difference in comparison with the starting value, which is set at 100%.

| Example No. | Concentration (g/l) | % change in the ventricular amplitude |
|---|---|---|
| 8 | $10^{-3}$ | −23% |
| 10 | $10^{-3}$ | −100% |
| 14 | $10^{-3}$ | −100% |
| 15 | $10^{-3}$ | −79% |
| 19 | $10^{-3}$ | −20% |
| 20 | $10^{-3}$ | −4% |

The new active compounds can be converted in a known manner into the customary formulations, such as tablets, dragees, pills, granules, aerosols, syrups, emulsions, suspensions and solutions, using inert nontoxic pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case of the use of water as the diluent, organic solvents can be used as auxiliary solvents if appropriate.

Examples of auxiliaries which may be mentioned are: water, non-toxic organic solvents, such as paraffins (for example petroleum fractions), vegetable oils (for example groundnut/sesame oil), alcohols (for example: ethyl alcohol and glycerol), carriers, such as, for example, natural rock powders (for example kaolins, aluminas, talc and chalk) and synthetic rock powders (for example highly disperse silicic acid and silicates), sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin - sulphite waste liquors, methylcellulose, starch and polyvinylpyrrolidone) and lubricants (for example magnesium stearate, talc, stearic acid and sodium laurylsulphate).

The administration is carried out in the customary manner, preferably orally or parenterally, in particular perlingually or intravenously. In the case of oral use, the tablets can of course also contain, in addition to the excipients mentioned, additives, such as sodium citrate, calcium carbonate and dicalcium phosphate, together with various additional substances, such as starch, preferably potato starch, gelatine and the like. Lubricants, such as magnesium stearate, sodium laurylsulphate and talc, can furthermore be co-used for tablet-making. In the case of aqueous suspensions, in addition to the abovementioned auxiliaries, various flavor correctants or dyestuffs can be added to the active compounds.

In the case of parenteral use, solutions of the active compounds can be employed, using suitable liquid excipients.

In general, it has proved advantageous in the case of intravenous administration to administer amounts of about 0.001 to 1 mg/kg, preferably about 0.01 to 0.5 mg/kg of body weight, in order to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular to do so as a function of the body weight or the nature of the administration route, the individual behaviour towards the medicament, the nature of its formulation and the time or interval at which administration takes place. Thus, in some cases it may suffice to manage with less than the abovementioned minimum amount, whilst in other cases the upper limit mentioned must be exceeded. Where relatively large amounts are administered, it may be advisable to divide these into several individual doses over the course of the day.

PREPARATION EXAMPLES

EXAMPLE 1

Dimethyl 1,4-dihydro-2,6-dimethyl-4-(2,2,3-trifluoro-1,4-benzodioxan-6-yl)-pyridine-3,5-dicarboxylate

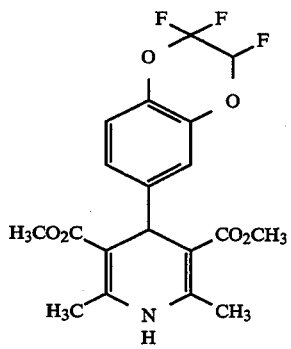

10 mmol of methyl acetoacetate, 10 mmol of methyl β-aminocrotonate and 10 mmol of 2,2,3-trifluoro-1,4-benzodioxan-6-yl-carbaldehyde are heated under reflux in 30 ml of methanol for 12 hours. After checking that the reaction is complete, some of the methanol is evaporated off. The product crystallizes out slowly with the addition of petroleum ether and trituration.

Yield: 59% of theory

Melting point: 227° C.

EXAMPLE 2

Methyl (2,2-difluoro-1,3-benzodioxol-5-yl)-methylene-acetoacetate

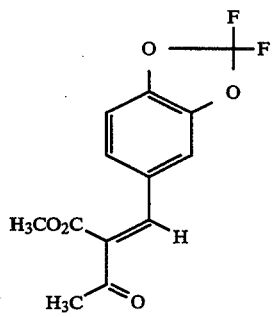

50 mmol of 5-(butyliminomethyl)-2,2-difluoro-1,3benzodioxole and 50 mmol of methyl acetoacetate are added simultaneously to 80 ml of acetic anhydride and, after brief warming, the mixture is left to stand at room temperature for 24 hours. It is then hydrolyzed with 1 l of ice-water and the oil which has separated out is separated off, diluted with a little methylene chloride, dried and subsequently used as the crude product.

EXAMPLE 3

Dimethyl 4-(2,2-difluoro-1,3-benzodioxol-5-yl)-1,4-dihydro-2,6-dimethyl-pyridine-3,5-dicarboxylate

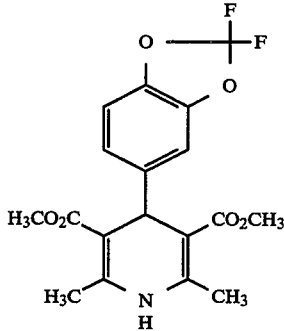

20 mmol of methyl β-aminocrotonate and 20 mmol of crude methyl (2,2-difluoro-1,3-benzodioxol-5-yl)-methylene-acetoacetate are heated under reflux in 30 ml of methanol for 12 hours, the methanol is evaporated off and the residue is chromatographed on silica gel with chloroform. The evaporated product fraction is taken up in a little methylene chloride and the mixture is foamed to a glass by rapid evacuation.

Melting point: resin
Yield: 69% of theory

EXAMPLE 4

Ethyl 2-[(2,2,3-trifluoro-1,4-benzodioxan-5-yl)-methylene]4-acetoxy-acetoacetate

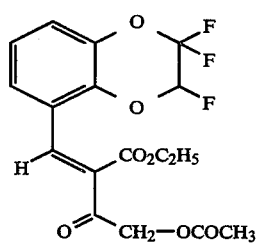

50 mmol of 5-(butyliminomethyl-2,2,3-trifluoro-1,4-benzodioxane and 50 mmol of ethyl 4-acetoxy-acetoacetate are stirred in 80 ml of acetic anhydride for 24 hours. The mixture is hydrolyzed with about 1 l of icewater and the oil which has separated out is separated off, taken up in methylene chloride, dried and used as the crude product.

EXAMPLE 5

Diethyl 2-acetoxymethyl-1,4-dihydro-6-methyl-4-(2,2,3-trifluoro-1,4-benzodioxan-5-yl)-pyridine-3,5-dicarboxylate

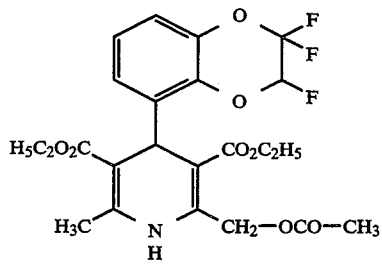

30 mmol of ethyl β-aminocrotonate and 35 mmol of crude ethyl 2-[2,2,3-trifluoro-1,4-benzodioxan-5-yl)methylene]-4-acetoxy-acetoacetate are heated under reflux in 50 ml of ethanol for 6 hours. The solvent is evaporated off and the residue is chromatographed on silica gel with chloroform/methanol. The evaporated product fractions are taken up in methylene chloride and the mixture is foamed to a glass by rapid evacuation.

Melting point: resin
Yield: 52% of theory

EXAMPLE 6

Ethyl 2-methyl-5-oxo-4-(2,2,3-trifluoro-1,4-benzodioxan-5yl)-1,4,5,7-tetrahydrofuro[3,4-b]pyridine-3-carboxylate

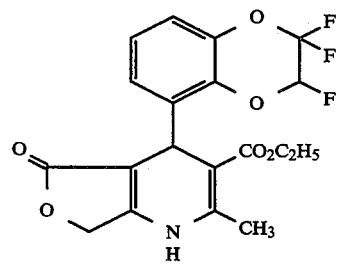

10 mmol of diethyl 2-acetoxymethyl-1,4-dihydro-6-methyl- 4-(2,2,3-trifluoro-1,4-benzodioxan-5-yl)-pyridine-3,5-dicarboxylate are heated in 25 mmol of ethanolic hydrochloric acid for 0.5 hour. The solvent is evaporated off and the residue is crystallized in a little ethanol with the addition of petroleum ether.

Melting point: 142° C.
Yield: 79% of theory

EXAMPLE 7

Methyl 4-(2,2-difluoro-1,3-benzodioxol-5-yl)-1,4-dihydro-6-methyl-5-nitro-pyridine-3-carboxylate

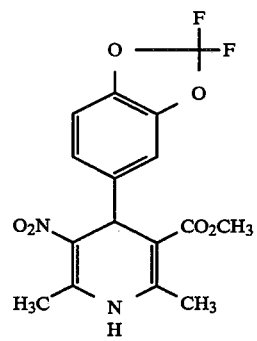

20 mmol of methyl (2,2-difluoro-1,3-benzodioxol-5-yl)-methylene-acetoacetate from Example 2 are heated under reflux in 30 ml of methanol with the addition of 2 ml of saturated methanolic ammonia solution, and 40 mmol of nitroacetone are added in portions. The mixture is heated under reflux for a further 6 hours, the solvent is evaporated off and the residue is chromatographed on silica gel with chloroform/methanol. After evaporation, the product fractions are taken up in methylene chloride and converted into a vitreous foam by rapid evacuation.

Melting point: resin
Yield: 48% of theory

The further examples in Table 1 were obtained analogously to Examples 1 to 7. The examples in Table 2 are obtained analogously to Example 1, 2 or 5.

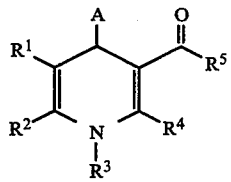

| Ex. no. | $R^1$ | $R^2$ | $R^3$ | $R^4$ | $R^5$ | A | m.p. [°C] |
|---|---|---|---|---|---|---|---|
| 8 | —COOCH$_3$ | —CH$_3$ | H | —CH$_3$ | —OCH$_3$ | (2,2,2-trifluoroethylidenedioxy-phenyl) | 227 |
| 9 | —COOCH$_3$ | —CH$_3$ | H | —CH$_3$ | —OCH$_3$ | (trifluoromethylenedioxy-phenyl) | 185 |
| 10 | —COOCH$_3$ | —CH$_3$ | H | —CH$_3$ | —OCH$_3$ | (1,1,2,2-tetrafluoroethylenedioxy-phenyl) | 219 |
| 11 | —COOCH$_3$ | —CH$_3$ | H | —CH$_3$ | —OCH$_3$ | (difluoromethylenedioxy-phenyl) | resin |
| 12 | —COOCH(CH$_3$)$_2$ | —CH$_3$ | H | —CH$_3$ | —OCH$_3$ | (tetrafluoroethylenedioxy-phenyl) | 133 |
| 13 | —COOC$_{10}$H$_{21}$ | —CH$_3$ | H | —CH$_3$ | —OCH$_3$ | (tetrafluoroethylenedioxy-phenyl) | resin |
| 14 | —COO—(CH$_2$)$_3$—C$_6$F$_{13}$ | CH$_3$ | H | —CH$_3$ | —OCH$_3$ | (difluoromethylenedioxy-phenyl) | resin |

-continued

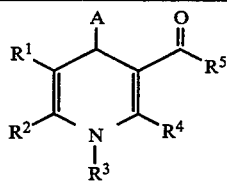

| Ex. no. | R¹ | R² | R³ | R⁴ | R⁵ | A | m.p. [°C.] |
|---|---|---|---|---|---|---|---|
| 15 | —COO—(CH₂)₃—C₆F₁₃ | —CH₃ | H | —CH₃ | —OC₂H₅ | benzo-dioxane with CF₂-CHF | resin |
| 16 | —COOC₂H₅ | —CH₃ | —CH₃ | —CH₃ | —OC₂H₅ | benzo-dioxane with CF₂-CHF | resin |
| 17 | —COO—CH₂ | | H | —CH₃ | —OC₂H₅ | benzo-dioxane with CF₂-CHF | 142 |
| 18 | —NO₂ | —CH₃ | H | —CH₃ | —OCH₃ | benzo-dioxane with CF₂-CHF | 189 |
| 19 | —NO₂ | —CH₃ | H | —CH₃ | —OCH₃ | benzo-dioxole with CF₂ | resin |
| 20 | —NO₂ | —CH₃ | H | —CH₃ | —OCH₃ | benzo-dioxane with CF₂-CHF | 223 |
| 21 | —NO₂ | —CH₃ | H | —CH₃ | —OCH₃ | benzo-dioxole with CF₂ | 173 |
| 22 | —NO₂ | —CH₃ | H | —CH₃ | —O—CH(CH₃)₂ | benzo-dioxole with CF₂ | 156 |
| 23 | —NO₂ | —CH₃ | H | —CH₃ | —CH₂CH₂CN | benzo-dioxane with CF₂-CHF | resin |

-continued

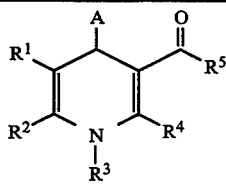

| Ex. no. | R¹ | R² | R³ | R⁴ | R⁵ | | A | m.p. [°C.] |
|---|---|---|---|---|---|---|---|---|
| 24 | —NO₂ | —CH₃ | —CH₃ | —CH₃ | —OH | | 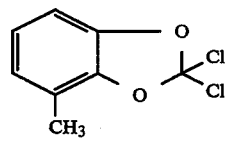 | 172 (decomp.) |
| 25 | —NO₂ | —CH₃ | H | —CH₃ | 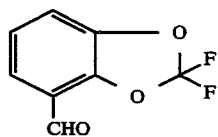 | | 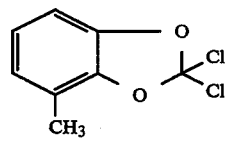 | 228 |
| 26 | —NO₂ | —CH₃ | H | —CH₃ | 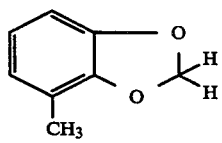 | | 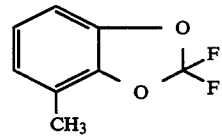 | 268 |

EXAMPLE 27

Synthesis of 2,2-difluoro-4-formyl-1,3-benzodioxole a) 4-Methyl-1,3-benzodioxole 400 g of methylene bromide and 50 g of tetrabutylammonium bromide are taken under reflux in a stirred apparatus and a solution of 400 ml of water, 130 g of sodium hydroxide and 200 g of 3-methylpyrocatechol are added dropwise in the course of 5 hours. At the end of the addition, the mixture is subsequently stirred for a further 2 hours, cooled and extracted with methylene chloride. The organic phase is dried and distilled on a column. After first runnings of unreacted methylene bromide, 175 g of 4-methyl-1,3-benzodioxole are obtained.

Boiling point: 94° C. (85 mbar)
n^D = 1.5218 b) 2,2-Dichloro-4-methyl-1,3-benzodioxole 160 g of 4-methyl-1,3-benzodioxole are added dropwise to 276 g of phosphorus pentachloride in 840 ml of carbon tetrachloride (prepared from phosphorus trichloride and chlorine), with stirring. Vigorous evolution of hydrogen chloride starts immediately. Towards the end of the reaction, 85 g of chlorine are passed in at about 20° C. and when the evolution of gas has ended, the mixture is then heated under reflux. By distillation, the phosphorus trichloride and carbon tetrachloride are recovered and the 4-methyl-2,2-dichloro-1,3-benzodioxole is then obtained at boiling point: 98°–99° C. (22 mbar).

Yield: 235 g c) 2,2-Difluoro-4-methyl-1,3-benzodioxole 200 ml of anhydrous hydrogen fluoride are taken in a fluorinating apparatus and 235 g of the chlorine compound 2,2-dichloro-4-methyl-1,3-benzodioxole are added dropwise at about 0° C. At the end of the addition, the mixture is warmed to 18°–20° C. and is subsequently stirred until the evolution of hydrogen chloride has ended. The excess hydrogen fluoride is then distilled over and the residue is stirred with sodium fluoride and filtered off with suction. The crude product is distilled over a rotating belt column and 142 g of 2,2-difluoro-4-methyl-1,3-benzodioxole are obtained.

Boiling point: 52°–54° C. (under 16 mbar)
$n_D^{20} = 1.4500$ d) 4-Bromomethyl-2,2-difluoro-1,3-benzodioxole

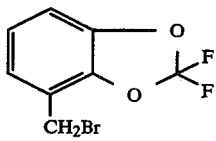

76 g of 2,2-difluoro-4-methyl-1,3-benzodioxole and 200 mg of Azobisisobutyronitrile are added to a suspension of 90 g of N-bromosuccinimide in 400 ml of methylene chloride. The mixture is then heated under reflux, with stirring, until all the undissolved material floats to the top. After cooling, the succinimide is filtered off with suction and rinsed with carbon tetrachloride and the solution is then distilled in order to separate off the carbon tetrachloride. 117 g of crude benzyl bromide remain in the residue and are employed without purification.

e) 2,2-Difluoro-4-formyl-1,3-benzodioxole

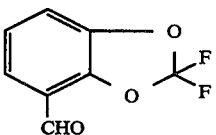

117 g of crude 4-bromomethyl-2,2-difluoro-1,3-benzodioxole are added to 120 g of urotropin in 250 ml of water and the mixture is heated under reflux for 3 hours. 120 ml of hydrochloric acid in 150 ml of water are then added and the mixture is heated for a further 3 hours. The crude product is then driven over with steam, removed from the receiver and shaken with 100 g of sodium bisulphate in 250 ml of water. After extraction with methylene chloride, the aqueous phase is acidified with 2 N sulphuric acid and the aldehyde is separated off and distilled. The yield is 53 g.

Boiling point: 99°–101° C. (under 18 mbar)
$n_D^{20} = 1.4875$

EXAMPLE 28

Synthesis of 2,2,3-trifluoro-6-formyl-1,4-benzodioxane

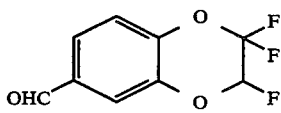

a) 2,2,3-Trifluoro-6-methyl-1,4-benzodioxane

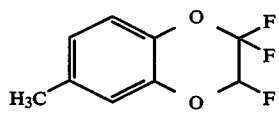

600 g of 4-methylpyrocatechol are taken in 1,500 ml of tetramethylenesulphone, and 500 g of potassium hydroxide are introduced in portions. 20 ml of water are added and the mixture is stirred at 110° C. until almost everything has dissolved, Difluorochloroethene is then passed up to saturation, with vigorous stirring, at the rate at which it is taken up. Steam is then passed in and the product is driven over. After the organic phase has been separated off and dried, it is distilled. 820 g of product are obtained.

Boiling point: 76°–80° C. (under 16 mbar),
$n_D^{20} = 1.4590$ (the product contains 2,3,3-trifluoro-6-methyl-1,4-benzodioxane as a by-product).

b) 6-Bromomethyl-2,2,3-trifluoro-1,4-benzodioxane / 6-dibromomethyl-2,2,3-trifluoro-1,4-benzodioxane

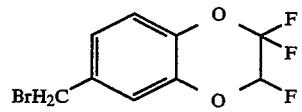

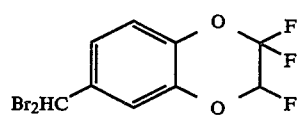

430 g of 2,2,3-trifluoro-6-methyl-1,4-benzodioxane are brominated in 3 1 of carbon tetrachloride with 750 g of N-bromosuccinimide and 5 g of Azobisisobutyronitrile Example 1d). 710 g of a mixture of mono- and dibromide are obtained.

Boiling point: 115°–118° C. (under 10 mbar)

c) 6-formyl -2,2,3-trifluoro-1,4-benzodioxane

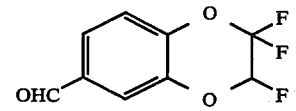

318 g of 6-bromo methyl-2,2,3-trifluoro-1,4-benzodioxane are added to 318 g of urotropin in 630 ml of water, the reaction mixture is heated under reflux for 2 hours, 3 18 ml of hydrochloric acid and 470 ml of water are then added and the mixture is heated for a further 3 hours. The product is driven over with steam and is separated off and, after drying, distilled. 158 g of distillate are obtained (boiling point: 112°–115° C. (under 18 mbar)) and partly crystallize on standing. The crystal sludge is filtered off with suction and the crystals are washed with cold petroleum ether.

Yield: 108 g of 2,2,3-trifluoro-6-formyl-1,4-benzodioxane.

Melting point: 92° C.

(The aldehyde is spectroscopically pure).

2,2,3-Trifluoro-6-formyl-1,4-benzodioxane can also be isolated from the filtrate by distillation on a rotating belt column.

Boiling point: 119°–120° C. (under 20 mbar)

EXAMPLE 29

Synthesis of 2,2,3,3-tetrafluoro-5-formyl-1,4-benzodioxane

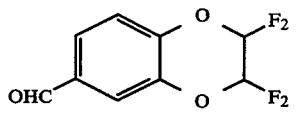

222 g of 5-amino-2,2,3,3-tetrafluoro-1,4-benzodioxane are taken in 800 ml of water and 250 ml of concentrated hydrochloric acid, the mixture is warmed to 80° C. and cooled rapidly to 0° C., with stirring, and diazotization is then carried out by dropwise addition of 69 g of sodium nitrite in 150 ml of water. The mixture is then subsequently stirred at 10° C. for one hour and at 20° C. for 20 minutes. 130 g of hydroxylamine hydrochloride and 60 g of paraformaldehyde in 400 ml of water are heated in a second stirred apparatus until a clear solution is formed. 235 g of sodium acetate, 40 g of copper sulphate and 13 g of sodium sulphite are then added, 800 g of ice are introduced and the mixture is then buffered with 500 g of sodium acetate. The diazonium salt solution initially prepared is added dropwise to this solution at 5°–10° C. At the end of the addition, the mixture is stirred at 20° C. for a further hour and then slowly heated to 100° C., and the product is driven over with steam. After the crude product has been separated off from the distillate, it is dried and redistilled over a rotating belt column. 108 g of aldehyde are obtained.

Boiling point: 85°–87° C. (under 14 mbar)
$n_D^{20} = 1.4685$

EXAMPLE 30

5-(Butyliminomethyl)-2,2-difluoro-1,3-benzodioxole

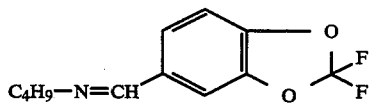

0.10 mol of 2,2-difluoro-5-formyl-1,3-benzodioxole are dissolved in 150 ml of methylene chloride, and 0.12 mol of n-butylamine is added at room temperature, with gentle cooling. The mixture is left to stand at room temperature for 20 hours, without stirring, the solvent is distilled off, together with the water which has separated out, under a slight vacuum, a further 150 ml of methylene chloride are added and are distilled off and the oil which remains is dried under an oil pump vacuum. The butylimino compound can be used in the crude form, for example in Example 2.

Butylimino compounds of other aldehydes according to the invention are prepared analogously to Example 28.

The compound of the formula

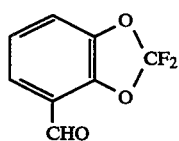

(II-a)

has an additional utility. In addition to the utilities expressed hereinabove, it can also be used to prepare the fungicidally active compound of the formula

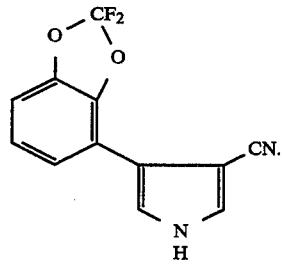

(A)

Such compound (A) can be synthesized in conventional manner (see EP-OS 0,182,738, EP-OS 0,206,999 and U.S. Pat. No. 4,680,413) by reacting the aldehyde of the formula (11-a) with α-cyano-acetic acid ethylester of the formula

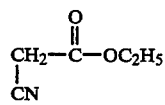

in the presence of an organic solvent and in the presence of a base, such as piperidine, and reacting the resulting nitrile compound of the formula

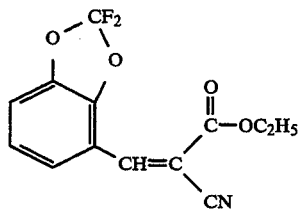

with p-toluene-sulphonyl-methyl isocyanide in the presence of an organic solvent and in the presence of a base, such as sodium hydride, sodium ethylate or potassium tert.-butylate.

It will be understood that the specification and examples are sllustrative but not limitative of the present invention and that other embodiments within the spirit and scope of the invention will suggest themselves to those skilled in the art.

We claim:
1. The 2,2-difluoro-4-formyl-1,3-benzodioxole of the formula

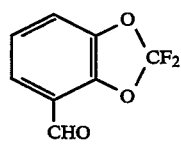

* * * * *